(12) United States Patent
Mezzenga et al.

(10) Patent No.: US 8,609,118 B2
(45) Date of Patent: Dec. 17, 2013

(54) SOLID OIL POWDERS

(75) Inventors: Raffaele Mezzenga, Preverenges (CH); Stephane Ulrich, Pully (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/125,230

(22) PCT Filed: Nov. 16, 2009

(86) PCT No.: PCT/EP2009/065229
§ 371 (c)(1),
(2), (4) Date: Apr. 20, 2011

(87) PCT Pub. No.: WO2010/057852
PCT Pub. Date: May 27, 2010

(65) Prior Publication Data
US 2011/0223225 A1    Sep. 15, 2011

(30) Foreign Application Priority Data
Nov. 19, 2008    (EP) .................................... 08169434

(51) Int. Cl.
*A61K 8/02*    (2006.01)
*A61K 9/00*    (2006.01)
*A61K 38/47*    (2006.01)

(52) U.S. Cl.
USPC .................... 424/401; 424/400; 424/94.61

(58) Field of Classification Search
USPC ............................................... 424/401
See application file for complete search history.

(56) References Cited

U.S. PATENT DOCUMENTS

| 4,921,705 | A | * | 5/1990 | Arai et al. ................... 424/450 |
| 5,776,490 | A | | 7/1998 | Chu et al. |
| 5,976,575 | A | * | 11/1999 | Gellenbeck ................ 424/489 |
| 5,976,604 | A | * | 11/1999 | Kunieda et al. ............. 426/602 |
| 7,374,788 | B2 | * | 5/2008 | Augustin et al. ............ 426/531 |
| 2001/0051204 | A1 | | 12/2001 | Cornelis et al. |
| 2007/0280979 | A1 | * | 12/2007 | Shinohara et al. .......... 424/401 |
| 2010/0074986 | A1 | * | 3/2010 | Bastiaans et al. ............. 426/2 |
| 2010/0285079 | A1 | * | 11/2010 | Imai et al. .................. 424/401 |

FOREIGN PATENT DOCUMENTS

| EP | 0372669 | 1/1990 |
| GB | 2240702 | 8/1991 |
| WO | WO9401001 | 1/1994 |
| WO | WO2007034213 | 3/2007 |
| WO | WO2008066380 | 6/2008 |

* cited by examiner

*Primary Examiner* — Robert T Crow
*Assistant Examiner* — Doan Phan
(74) *Attorney, Agent, or Firm* — K&L Gates LLP

(57) ABSTRACT

The present invention relates in general to the field of oil powders. In particular, the present invention relates to an oil composition that is in powder form at room temperature. One embodiment of the present invention is a solid oil powder that has a very high oil content.

19 Claims, 6 Drawing Sheets

SOLID OIL POWDERS

The present invention relates in general to the field of oil powders. In particular, the present invention relates to an oil composition that is in powder form at room temperature. One embodiment of the present invention is a solid oil powder that has a very high oil content.

Solidification of oil-in water emulsions is a technique that is employed in the pharmaceutical, cosmetic and food industry to reduce a liquid-oil base into a solid-like powder. The most diffused method is spray drying the emulsion to rapidly evaporate the water continuous phase (Faldt, P. et al. *Food Hydrocolloids*, 10, 421 (1996), Vega C. et al. *Food Hydrocolloids*, 45, 66 (2005), Fuchs, M. et al. *J. Food Engineering*, 75, 27 (2006), Bruckner, M. et al. *European Food, Research. And Technology*, 226, 137 (2007), Baranauskiene, R. et al. *J. Agric. Food Chem.*, 55, 3027 (2007)). This method is typically used to encapsulate hydrophobic compounds and aroma into the oil droplets or to increase stability of oil against oxidation (Klinkesorn, U. et al. *J. Agric. Food Chem.*, 53, 8365 (2005), Gu, Y. S. et al. *J. Agric. Food Chem.*, 52, 3626 (2004), Shaw, L. A. et al. *J. Agric. Food Chem.*, 55, 3112 (2007)). In order to prevent the oil droplets to collapse into a macro-phase separated liquid state during the spray drying processing at the first stage and during the shelf-life of the power afterwards, a solid hydrophilic carrier is normally added to the water solution. After water has evaporated, this hydrophilic carrier, together with the surfactant used to stabilize the liquid emulsion, constitute the continuous phase of the powder, also referred to as "solid dry base". The minimum amount of solid hydrophilic carrier needed varies from study to study but it is in general comprised between 30 and 80 weight-% of the total dry base (Klinkesorn, U. et al. *J. Agric. Food Chem.*, 53, 8365 (2005), Gu, Y. S. et al. *J. Agric. Food Chem.*, 52, 3626 (2004), Jost, R. et al. *Food Microstructure*, 8, 23 (1989)). Typical examples of the constituents of the solid dry base are lactose, glucose, maltodextrin, starch and cellulose. The presence of this hydrophilic carrier in the formulation alters the composition of the powder with respect the original emulsion, concentrating the solid carrier into the final powder, and thus reducing the amount of liquid dry base (the oil droplets). Without the presence of this solid carrier, however, the emulsion droplets coalesce either during the spray drying processing or afterwards, leading to the collapse of the powder and the leaking of the oil.

A possible alternative way to the introduction of this solid carrier, is the stabilization of the oil droplets interfaces in a physico-chemical way in order to provide enough elasticity to the interfaces to survive the spray drying process. A typical example is the multi-step deposition onto the droplets surfaces of positively charged polyelectrolytes capable to crosslink by ionic complexation, thus providing to the interfaces the need elasticity (Klinkesorn, U. et al. *J. Agric. Food Chem.*, 53, 8365 (2005), Gu, Y. S. et al. *J. Agric. Food Chem.*, 52, 3626 (2004), Moreau, L. et al. *J. Agric. Food Chem.*, 51, 6612 (2003)). A typical example would be to stabilize an oil-in water emulsion by a protein and to adjust the solution pH to acidic enough values to positively charge the protein. Then the emulsion is dialyzed or diluted with another water solution containing a negatively charged polyelectrolyte capable to ionically complex with the positively charged oil droplets interfaces (made positive by the protein layer). Another variant is to stabilize the droplets by a low molecular weight anionic surfactant such as lecithin and then expose the emulsion to a polycationic polysaccharide, such as chitosan. Although this is generally considered a reliable method, the main drawback of this approach is that multiple steps are needed to stabilize the droplet surfaces, which makes this technology rather expensive and unsuitable for large scale processing. Thermal (Romoscanu, A. I. et al. *Langmuir*, 21, 9689 (2005)) or enzymatic cross-linking (Kellerby, S. S. et al. *J. Agric. Food Chem.*, 54, 10222 (2006), Cho, Y. H. et al. *Journal of Food Science*, 68, 2717, (2003)) of the protein-stabilized interface is another efficient method to provide elasticity to the interface. Thermal cross link of whey protein stabilized oil-in water emulsion has been employed using rather large excess of protein, in combination with spray drying, to lead to a dry oil powder. The calculated amount of protein in the final powder is, however, still of the order of 28-30 weight-% of the total powder.

To summarize, dried solid oil powders comprising oily compounds that are usually liquid at room temperature are available today only in formulations, which comprise a relatively high weight percentage of non-oily compounds. Having available at room temperature a dry solid oil powder comprising a very high percentage of oily compounds or even consisting essentially of oily compounds would bring about several significant advantages, such as simpler formulations, absence of water-transport layers, increased hydrophobic encapsulation efficiency, etc. Consequently, there is a need in the art for such solid oil powders.

Hence, it was the object of the present invention to provide the art with a solid oil powder that comprises a higher weight percentage of oily compounds than the powders of the prior art and with possible applications of such a solid oil powder. It was also an object of the present invention to provide the art with a method to produce such a solid oil powder.

The present inventors were surprised to see that they could achieve these objects by a powder in accordance with claim 1 and by a use in accordance with claim 10 and by a method in accordance with claim 15.

The inventors have used protein stabilized oil-in-water emulsions, thermal cross-linking and spray drying techniques to achieve, for example, in a one-step process, solid oil powders in which the total amount of oil can be easily made for example as high to 95% by weight, and possibly as high as 99%, without compromising the solid nature of the powder.

In other terms, it is now possible to encapsulate at least 95% oil with only 5% solid matrix, without affecting the dry powder nature. Upon evaporation of water, and removing eventual excess of unabsorbed protein, the solid dry base is simply given by the protein cross-linked around the droplet surfaces (typically 1% or less), and the optional presence of salt (typically 5% or less and only if the emulsion is spray dried from a buffer salt solution).

Consequently, one embodiment of the present invention is an oil powder that is solid at room temperature and that comprises at least 90 weight-%, preferably at least 95 weight-%, even more preferred at least 99 weight-% oil.

A powder is a bulk, granular solid composed of a large number of fine particles that may flow freely when shaken or tilted.

The oil powder of the present invention is preferably a dry powder. For the purpose of the present invention is an oil powder considered as dry, if no more than 1 weight-% of oil—and preferably no oil—is leaking out of the oil powder at room temperature, if the oil powder is stored at room temperature for 24 hours without exceeding the normal atmospheric pressure.

The oil powder of the present invention is considered as solid if the powder particles that comprise the possibly liquid oil retain their individual three-dimensional structure and are not "melting".

The solid oil powders of the present invention have for example the advantages that they can be produced with a very simple and efficient procedure, for example a one-step-process, that they can be produced with very high oil contents, that they do not require a solid dry base as the powders of the prior art, and that the can be produced with only protein as additive and optionally with salt, which is both skin friendly, natural and generally even food grade.

A solid oil powder comprising 90 weight-% oil, for example, may comprise up to 10 weight-% protein.

Typically, however, will a solid oil powder according to the present invention comprise a maximum of 1 weight-% protein and/or a maximum of 5 weight-% salt. The oil powder in accordance with the present invention, in particular the individual particles of the powder, may comprise an inner core comprising the oil fraction and an outer shell comprising cross-linked protein.

The amount of protein and/or salt used may be adjusted to fine tune the stability of the particles. Usually, the particles are meant to release their oil content under pressure. The amount of protein and/or salt used along with the degree of crosslinking of the protein shell of the powder particles will determine the amount of pressure needed to release the oil.

Alternatively and/or simultaneously the particles may also be designed to release their oily content upon application of heat. Heat application will cause the oil to expand, which will ultimately lead to a disruption of the protein shell around the oil fraction. The thicker the protein membrane is the more heat will be needed to liberate the oil from the shell.

The oils that can be used in accordance with the present invention are not particularly limited. The term "oil" comprises for the purpose of the present invention mineral oils, and/or organic oils (oils produced by plants or animals), in particular food grade oils and/or oils for cosmetic applications. Typical mineral oils comprise paraffinic oils (based on n-alkanes), naphthenic oils (based on cycloalkanes), and aromatic oils (based on aromatic hydrocarbons).

The food grade oil and/or oil for cosmetic applications may for example be selected from the group consisting of olive oil, safflower oil, sunflower oil, fish oil, soy bean oil, soy oil, palm kernel oil, palm oil, coconut oil, flaxseed oil, rapeseed oil, primrose oil, essential oils, animal oil, mineral oils, organic oil and combinations thereof.

An essential oil is a concentrated, hydrophobic liquid containing volatile aroma compounds, for example from plants. They are also known as volatile or ethereal oils. An oil is "essential" in the sense that it carries at least one scent, or essence, for example of a plant. Essential oils are often used in cosmetic applications to produce a fragrance.

The protein that is used to encapsulate the oil to produce the dry powder of the present invention may be any protein. For food and cosmetic applications it is preferred if the protein is a food grade protein and/or a protein that provides additional benefits to the consumer, for example in terms of taste, texture, and/or anti-allergenicity.

For example milk- and/or whey derived proteins are preferred.

Preferred milk proteins or milk protein fractions in accordance with the present invention comprise whey proteins, α-lactalbumin, β-lactoglobulin, bovine serum albumin, acid casein, caseinates, α-casein, β-casein, κ-casein, for example.

As far as whey proteins are concerned, the protein source may be based on acid whey or sweet whey or mixtures thereof and may include alpha-lactalbumin and beta-lactoglobulin in whatever proportions are desired. The proteins may be intact or at least partially hydrolysed. It may be desirable to use partially hydrolysed proteins (for example with a degree of hydrolysis between 2 and 20%), for subjects that are believed to be at risk of developing cows' milk allergy.

A material is food-grade if it is approved for human or animal consumption.

Hence in one embodiment of the present invention, the protein may comprise comprise α-lactalbumin, β-lactoglobulin, bovine serum albumin, acid casein, caseinates, α-casein, β-casein, κ-casein, egg albumen, lysozyme, soy proteins, gluten, rice proteins, corn proteins, potato proteins, pea proteins, or any kind of globular and random coil proteins or combinations thereof.

The salt that may be used in accordance with the present invention is equally not particularly limited. Preferred are alkali metal salts or earth alkali metal salts.

It may be preferable to use food-grade salts.

For example, the oil powder may comprise sodium citrate, magnesium citrate, potassium citrate, or combinations thereof.

The oil powder of the present invention may be used for example as a vehicle to deliver valuable compounds. For example, the oil may contain such a valuable compound.

Hence, in one embodiment of the present invention the oil may contain at least one liposoluble compound, such as for example a plant polyphenols, a fatty acid, such as DHA, n-3 fatty acids such as α-linolenic acid, stearidonic acid, eicosatrienoic acid, eicosatetraenoic acid, eicosapentaenoic acid, docosapentaenoic acid, clupanodonic acid, docosahexaenoic acid, tetracosapentaenoic acid, or tetracosahexaenoic acid, n-6 fatty acids such as linoleic acid, gamma-linolenic acid, eicosadienoic acid, dihomo-gamma-linolenic acid, arachidonic acid, docosadienoic acid, adrenic acid, docosapentaenoic acid or calendic acid, a vitamin, an aroma compound, an antioxidant, or another active ingredient.

The single particles of the oil powder of the present invention may have any size depending only on the intended use of the powder. Larger particles will allow reducing the amount of protein necessary to encapsulate the oil even further. Smaller particles will in general have a greater stability and will allow a more exact dosability. Typical particle diameters of the oil powder in accordance with the present invention may be in the range of about 0.1-100 μm, for example about 1 to 50 μm.

The oil powder of the present invention may be used in a number of different applications.

For example, the oil powder may be used for the production of a composition, wherein preferably, the composition is selected from the group consisting of a lubricant, a food composition, a food additive, a nutraceutical, a pharmaceutical composition and/or a cosmetic composition.

Such a composition has the advantage that it may be used to protect the oil and/or the liposoluble compounds contained therein, for example from influences that reduce the quality of the composition such as oxidative damage.

It may also be used to prolong the possible storage times of the oils and/or of the liposoluble compounds.

Such compositions comprising the oil powder of the present invention will furthermore provide an improved flowability and/or an improved dosability of the oils and/or of the liposoluble compounds that may be contained therein.

The composition and/or the oil powders of the present invention may be used to provide a powder that is re-dispersable in water as a single primary emulsion.

Primary emulsions are two-phase systems in which a phase, such as oil, is dispersed in another phase, such as water. These emulsion are referred to as primary oil-in-water emulsions. By dispersing water in an oil matrix, one will refer to these systems as water-in-oil primary emulsions.

As such, the powder of the present invention may conveniently be used to produce emulsions in hydrophilic solvents, such as water, for example, simply by adding the powder to the hydrophilic solvent and by agitating.

The powder of the present invention has the advantage that it can be used to bring oil into contact, for example, with the skin or with another surface, while it can be avoided that an oil film is left behind, for example, on a device that is used to apply the oil. Further, accidental spills of the powder of the present invention can be easily swept away without the need to use detergents to remove an oil film.

Oil is released from the powder of the present invention only by applying stress to the individual particles, so that the protein shell is bursting and the at least one oil is set free.

Hence, the oil powder can release liquid oils for example upon sharing, compression, shaking, squeezing, spreading or combination thereof.

The present invention further extends to a method to prepare an oil of the present invention.

Such a method comprises the steps of
mixing the oil, the protein and optionally the salt, and/or at least one liposoluble compound to prepare an emulsion,
cross-link the protein,
spray dry the emulsion to generate the oil powder.

The protein may be crosslinked by any method that is known in the art, for example by UV-radiation, chemically, enzymatically or by heat application for example by elevating the temperature to at least 70° C. for at least 5 minutes.

Those skilled in the art will understand that they can freely combine all features of the present invention described herein, without departing from the scope of the invention as disclosed. In particular, features described for the uses of the present invention may be applied to the powder and to the composition of the present invention and vice versa.

Further advantages and features of the present invention are apparent from the following Examples and Figures.

FIG. 1 shows the parent size distribution of a 10% olive oil-in-water emulsion stabilized by 1% β-lactoglobulin, prior and after the cross-linking process.

FIG. 2A shows the aspect of the resulting spray dried powder (after 15 minutes at 80° C. heat denaturation of the protein at the interface) from the emulsion described in FIG. 1. The spray drying was done in a Büchi 190 mini spray dryer (temperature inlet 125° C., outlet 84° C.).

Figure 2:
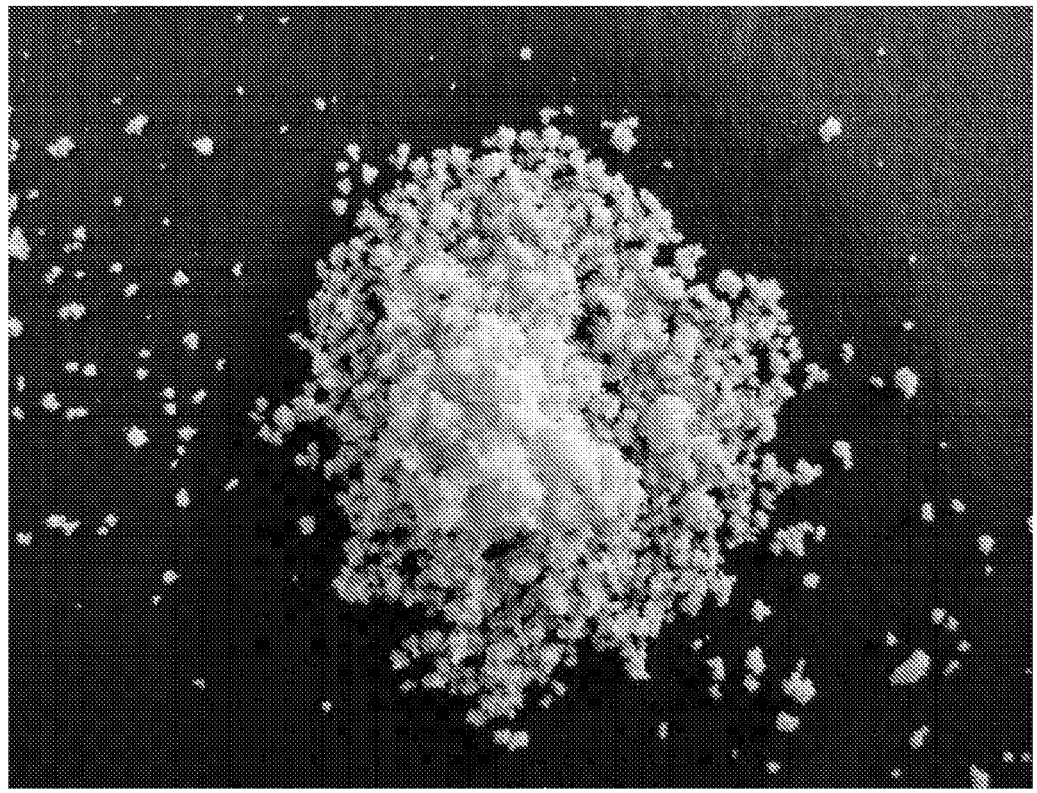
FIG. 2B shows the same powder of FIG. 2A, as observed by Bright field light microscopy.
FIG. 2C shows the same powder of FIG. 2A, as observed by UV Light Microscopy (excitation: BP450-490, emission LP 520, Nile Red staining, Mounting agent: glycerol 40%).
Figure 2:
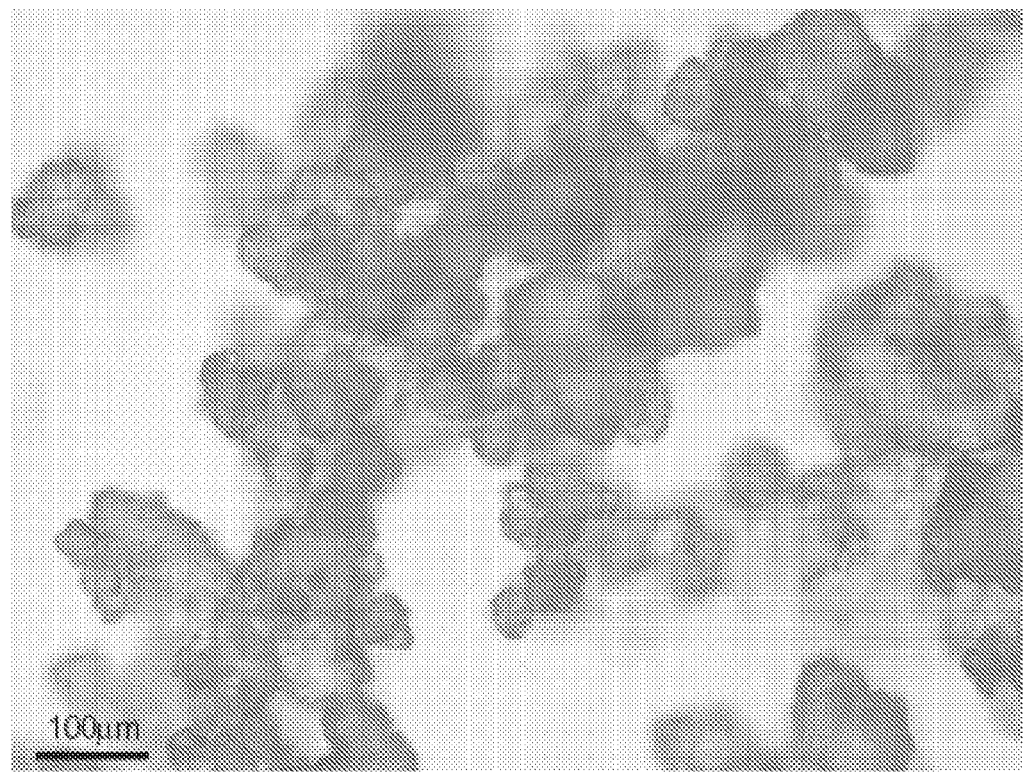
Figure 2C:
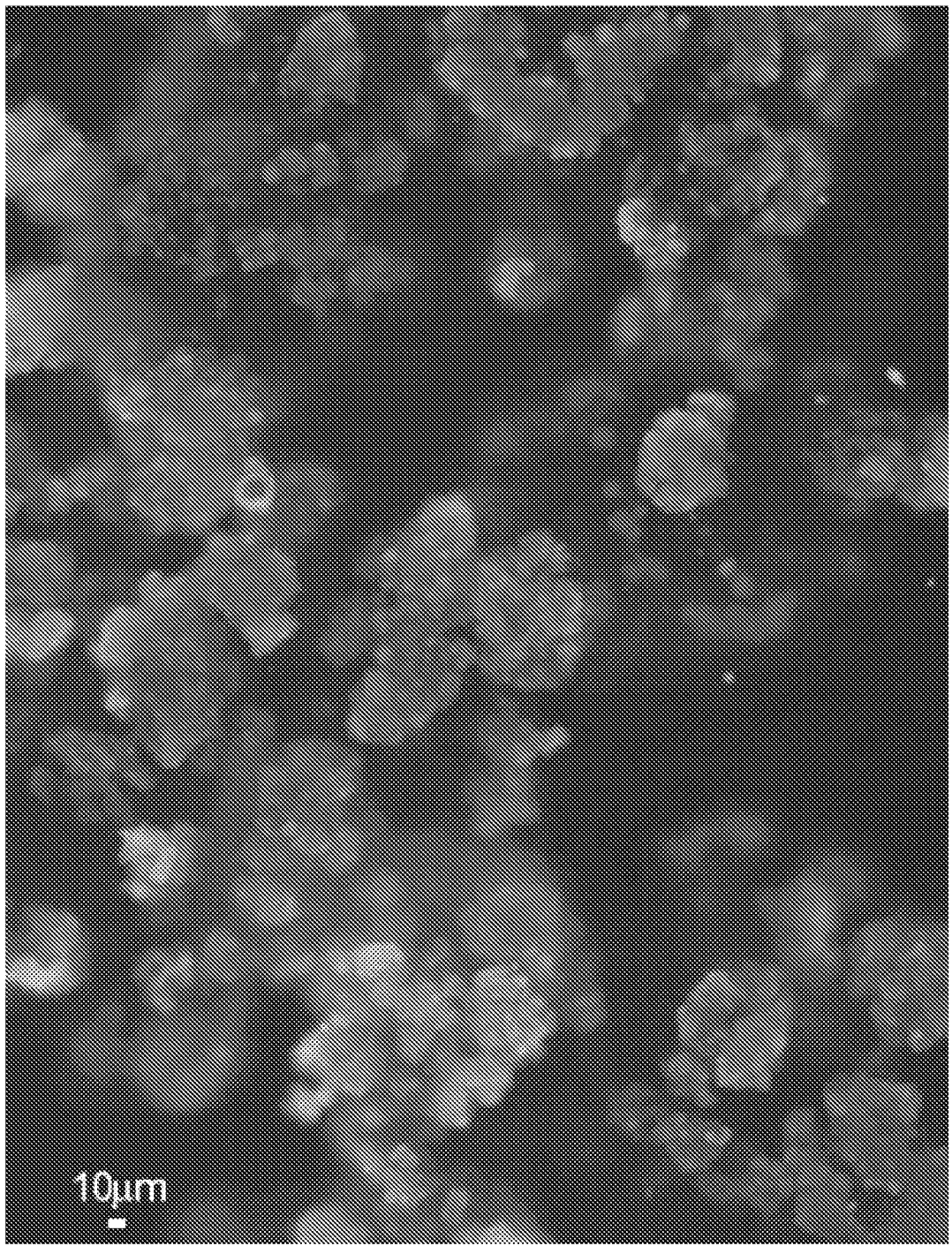
Figure 2D:
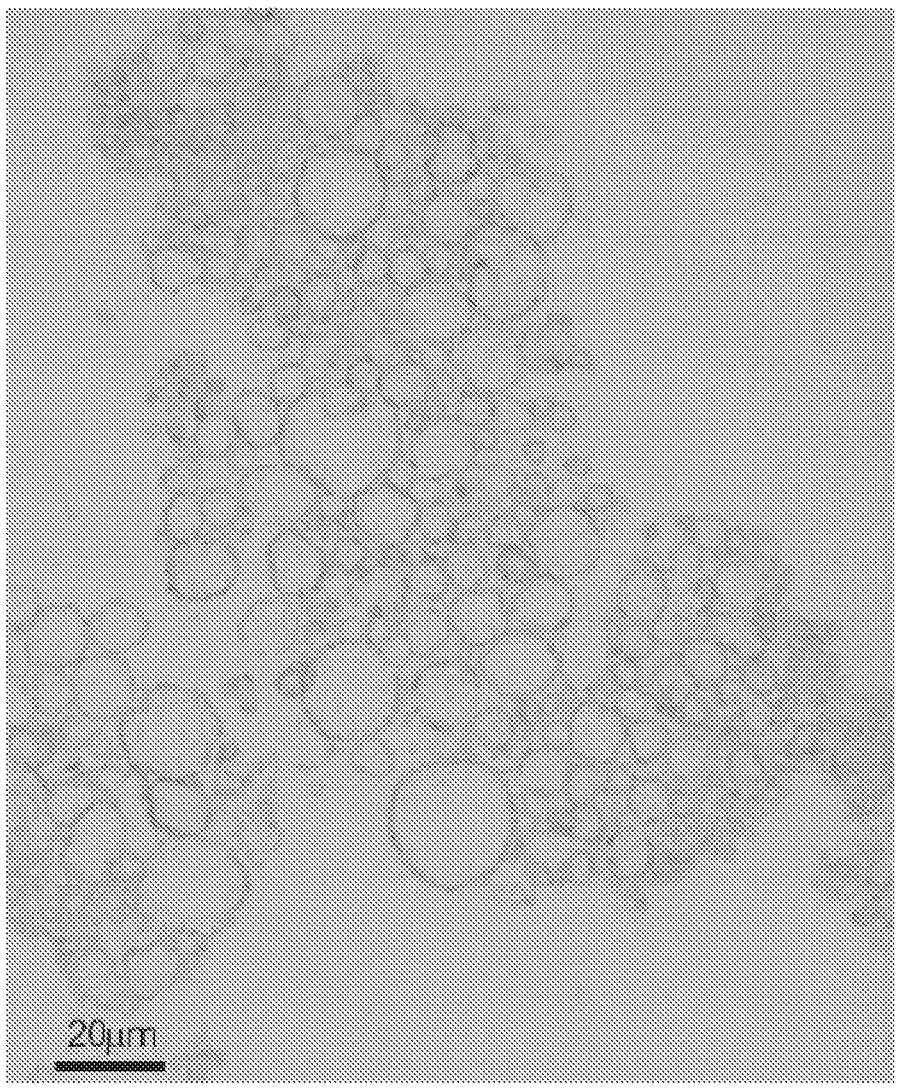

FIG. 2D shows the same powder of FIG. 2A, as observed by Bright Field Light Microscopy (Protein Staining). Cryofixation: anhydrous Glutaraldehyde/Osmium tetraoxide in methanol. Embedding: Spurr. Thin sections 1 micron: Staining: Toluidine blue.

Figure 2E:
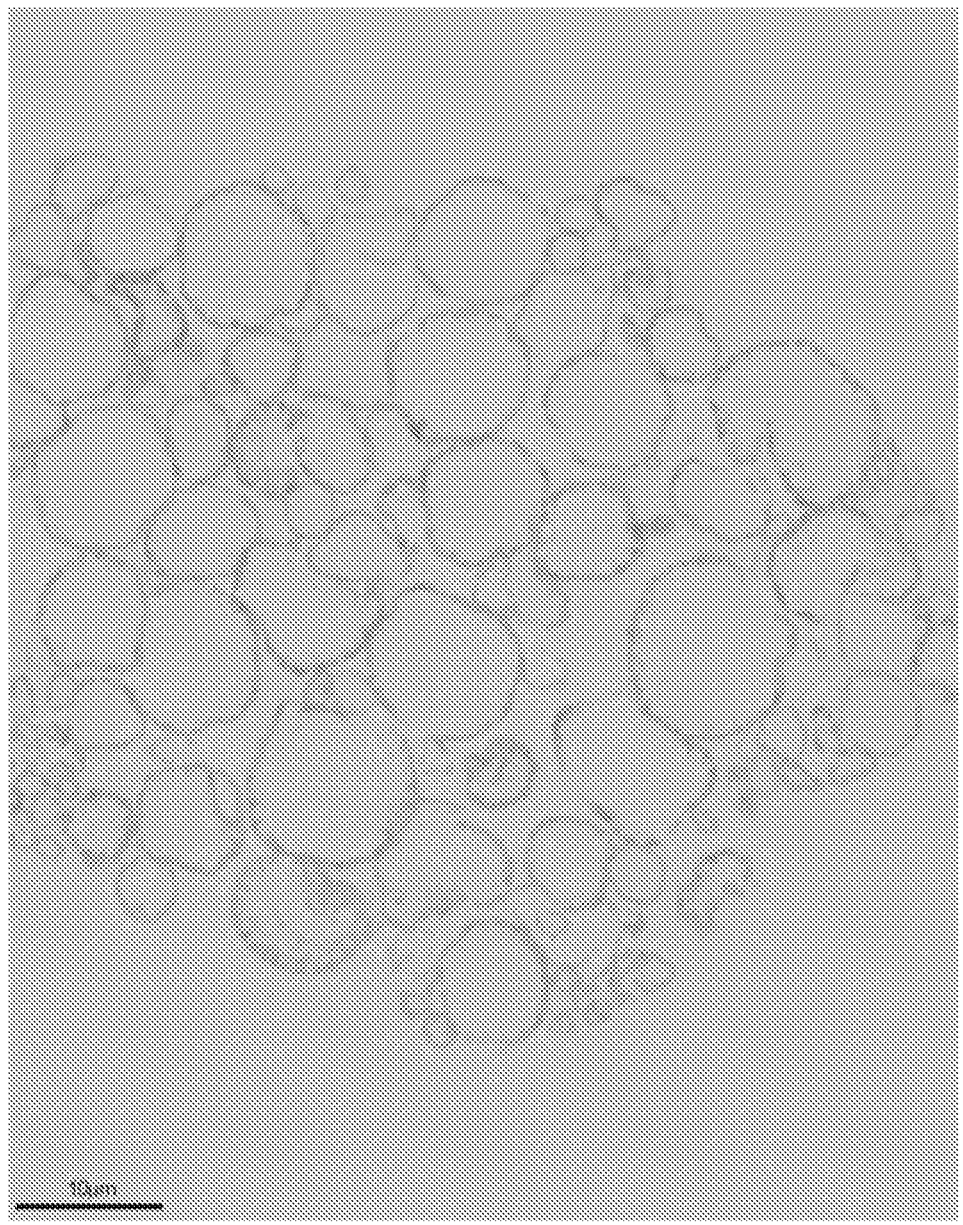

FIG. 2E shows the same powder of FIG. 2A, as observed by Bright Field Light Microscopy (Protein Staining) Cryofixation: anhydrous Glutaraldehyde/Osmium tetraoxide in methanol. Embedding: Spurr. Thin sections 1 micron: Staining: Toluidine blue. (Higher magnification compared to FIG. 2D).

Figure 3:
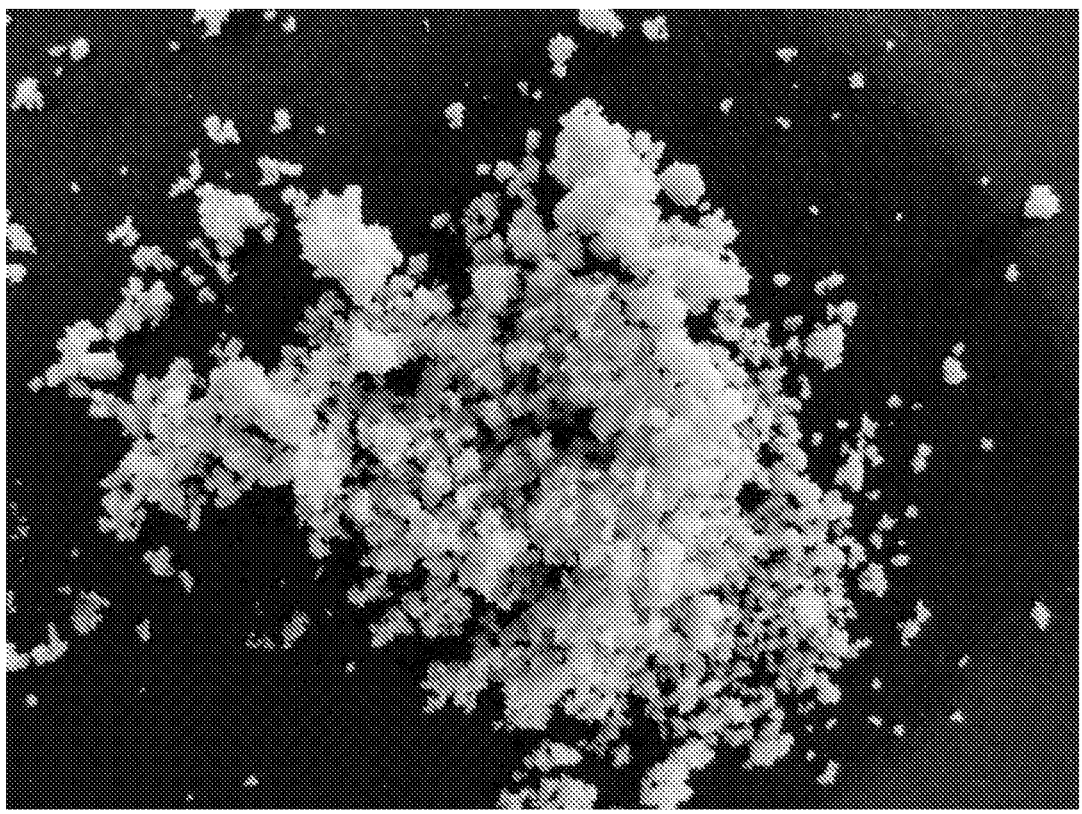

FIG. 3 shows the aspect of a spray dried powder (after 15 minute at 80° C. heat denaturation of the protein at the interface) from a 10% olive oil-in-water emulsion stabilized by 4% soy protein (spray drying was done in a Büchi 190 mini spray dryer (temperature inlet 125° C., outlet 84° C.).

EXAMPLE 1

Spray Dried Olive Oil Powder (with Beta-Lactoglobulin Protein)

Figure 1:
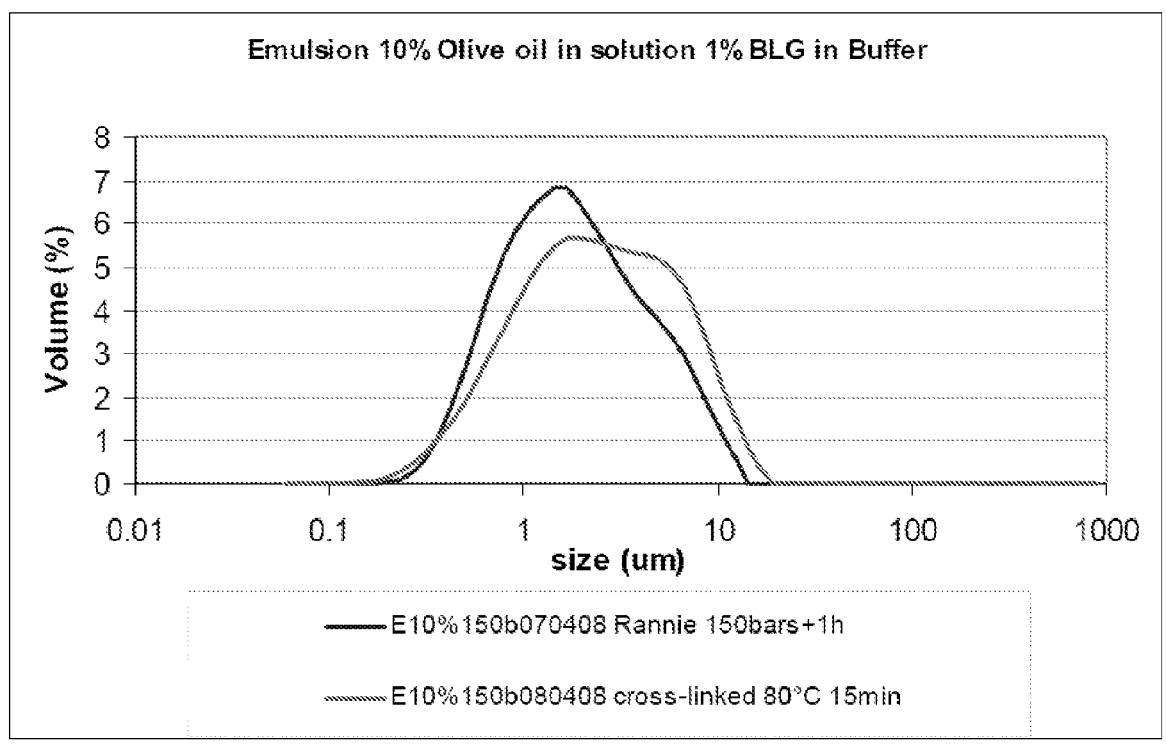

Preparation of Solution
Sol A: Prepare a 20 mM of tri-sodium citrate buffer solution (11.764 g/2l)
Sol B: Prepare a solution of 1% Beta-lactoglobulin (Davisco 92%) in the buffer (10.835 g Blg/1l buffer) pH=7.3
Characterization Method for the Emulsion
Weigh 270 g of sol 1% beta-lactoglobulin+30 g olive oil (N° Cas=8001-25-0).
Mix it with a polytron position 4 during 45 sec.
Pass trough a high pressure homogenizer at 150 bars (Rannie), to obtain a 10%
Emulsion Olive oil in 1% Blg buffer solution
Analyze it in a particle sizer (Malvern)
Cross link the 10% olive oil emulsion during 15 minute at 80° C.
Cool down and analyze it in a particle sizer (Malvern)
Results are shown in FIG. 1 and in Table 1.
Table 1 shows the characteristic or the parent emulsion as studied by a Malvern Mastersizer.

| D [4.3]/ um | D [3.2]/ um | D (v, 0.5)/ um | D (v, 0.1)/ um | D (v, 0.9)/ um | Span | Residual/ % |
|---|---|---|---|---|---|---|
| E10% 150b070408 Rannie 150 bars + 1 h | | | | | | |
| 2.37 | 1.21 | 1.60 | 0.57 | 5.44 | 3.05 | 0.54 |
| E10% 150b080408 cross-linked 80° C. 15 min | | | | | | |
| 3.17 | 1.40 | 2.19 | 0.63 | 7.19 | 3.00 | 0.33 |

Spray Drying
Spray dry the 10% crosslinked Emulsion in a Büch 190 mini spray dryer (temperature inlet 125° C., outlet 84° C.).
The obtained dry oil powder was analyzed by
Powder aspect,
Brightfield light microscopy,
UV Light Microscopy (excitation: BP450-490, emission LP 520) Nile Red staining Mounting agent: glycerol 40%
Bright Field Light Microscopy (Protein Staining) Cryofixation: anhydrous Glutaraldehyde/Osmium tetroxide in methanol. Embedding: Spurr. Thin sections 1 micron: Staining: Toluidine blue.
Bright Field Light Microscopy (Protein Staining)
Cryofixation: anhydrous Glutaraldehyde/Osmium tetroxide in methanol.
Embedding: Spun. Thin sections 1 micron: Staining: Toluidine blue.
Results are shown in FIG. 2.

EXAMPLE 2

Spray Dried Olive Oil Powder with Soy Proteins

Solution
Sol A: Prepare a 20 mM of tri-sodium citrate buffer solution (11.764 g/2l)
Sol B: Prepare a solution of 4% soy protein (Solpro 958 90%) in the buffer (17.6 g Blg/382.4 g buffer) by controlling the pH at 8 with NaOH 1M
Method Centrifuge the solution B at 5000 rpm during 30 min and then filter it at 0.2 μm Weight 270 g of this solution+30 g olive oil (N° Cas=8001-25-0).

Mix it with a polytron position 4 during 45 sec.

Then submit to sonication at 70% position 1 3× 1 min (3 times)

Analyze it in a particle sizer (Malvern)

Cross-link the 10% olive oil emulsion 15 minute at 80° C.

Analyze it in a particle sizer (Malvern) when it's cold

The results are shown in table 2:

TABLE 2

| D [4.3]/ um | D [3.2]/ um | D (v, 0.5)/ um | D (v, 0.1)/ um | D (v, 0.9)/ um | Span | Residual/ % |
|---|---|---|---|---|---|---|
| E10% olive oil with soya 090706 (sonication 3 × (3 × 1 min)) | | | | | | |
| 2.90 | 1.44 | 2.03 | 0.67 | 6.45 | 2.84 | 0.79 |
| E10% olive oil with soya 090706 cross-linked 80° C. 15 min | | | | | | |
| 2.87 | 1.48 | 1.97 | 0.70 | 6.34 | 2.86 | 0.26 |

Then spray dry the 10% crosslinked Emulsion in a Büch 190 mini spray dryer (temperature inlet 126° C., outlet 84° C.).

The resulting solid oil powder is shown in FIG. 3.

The invention claimed is:

1. Oil powder that is solid at room temperature and comprises at least 90 weight-% oil.

2. Oil powder in accordance with claim 1, comprising a maximum of 1 weight-% protein.

3. Oil powder in accordance with claim 1, comprising an inner core comprising an oil fraction and an outer shell comprising cross-linked protein.

4. Oil powder in accordance with claim 1, wherein the oil comprises an oil selected from the group consisting of mineral oils and organic oils.

5. Oil powder in accordance with claim 1, wherein the oil is selected from the group consisting of olive oil, safflower oil, sunflower oil, fish oil, soy bean oil, soy oil, palm kernel oil, palm oil, coconut oil, flaxseed oil, rapeseed oil, primrose oil, essential oils, animal oil, mineral oils and combinations thereof.

6. Oil powder in accordance with claim 1, comprising at least one food-grade protein.

7. Oil powder in accordance with claim 1, comprising food-grade salts.

8. Oil powder in accordance with claim 1, wherein the oil contains at least one liposoluble compound.

9. Oil powder in accordance with claim 1, wherein the oil powder has an average particle size in the range of about 0.1-100 μm.

10. A method for producing a composition selected from the group consisting of a lubricant, a food composition, a food additive, a nutraceutical, a pharmaceutical composition and a cosmetic composition comprising producing the composition using an oil powder that is solid at room temperature and comprises at least 90 weight-% oil.

11. Method in accordance with claim 10, wherein the method protects oil and/or liposoluble compounds from oxidative damage.

12. Method in accordance with claim 10, wherein the method provides an improved flowability of the oils.

13. Method in accordance with claim 10, wherein the method provides a powder that is re-dispersable in water as a single primary emulsion.

14. Method in accordance with claim 10, comprising the step of releasing liquid oils from the oil powder upon shearing, compression, shaking, squeezing, spreading or any combination thereof.

15. Method to prepare an oil powder comprising the steps of
    mixing an oil and protein to prepare an emulsion,
    cross-linking the protein, and
    spray dry the emulsion to generate an oil powder that is solid at room temperature and comprises at least 90 weight-% oil.

16. Oil powder that is solid at room temperature and comprises at least 99 weight-% oil.

17. Oil powder in accordance with claim 1, comprising a maximum of 5 weight-% salt.

18. Method in accordance with claim 15, wherein the step of cross-linking the protein is achieved by elevating the temperature to at least 70° C. for at least 5 minutes.

19. Oil powder in accordance with claim 1 comprising at least 95 weight-% oil.

* * * * *